(12) United States Patent
Sekiguchi

(10) Patent No.: US 8,125,514 B2
(45) Date of Patent: Feb. 28, 2012

(54) ELECTRONIC ENDOSCOPE APPARATUS

(75) Inventor: Tadashi Sekiguchi, Saitama (JP)

(73) Assignee: Fujinon Corporation, Saitama (JP)

( * ) Notice: Subject to any disclaimer, the term of this patent is extended or adjusted under 35 U.S.C. 154(b) by 1154 days.

(21) Appl. No.: 11/862,247

(22) Filed: Sep. 27, 2007

(65) Prior Publication Data

US 2008/0079803 A1 Apr. 3, 2008

(30) Foreign Application Priority Data

Sep. 29, 2006 (JP) ................. P 2006-267104

(51) Int. Cl.
*A61B 1/04* (2006.01)
(52) U.S. Cl. ............... 348/45; 348/58; 348/71; 382/128
(58) Field of Classification Search .............. 348/45, 348/60
See application file for complete search history.

(56) References Cited

U.S. PATENT DOCUMENTS

| | | | | |
|---|---|---|---|---|
| 5,515,449 | A * | 5/1996 | Tsuruoka et al. | 382/128 |
| 7,525,704 | B2 * | 4/2009 | Loce et al. | 358/540 |
| 7,800,656 | B2 * | 9/2010 | Takeuchi et al. | 348/222.1 |
| 7,944,466 | B2 * | 5/2011 | Abe et al. | 348/71 |
| 2001/0024231 | A1 * | 9/2001 | Nakamura et al. | 348/58 |
| 2003/0067539 | A1 * | 4/2003 | Doerfel et al. | 348/51 |
| 2006/0197830 | A1 | 9/2006 | Takeuchi et al. | |
| 2006/0211915 | A1 | 9/2006 | Takeuchi et al. | |
| 2008/0079803 | A1 * | 4/2008 | Sekiguchi | 348/45 |

FOREIGN PATENT DOCUMENTS

| | | |
|---|---|---|
| EP | 1 302 152 A1 | 4/2003 |
| EP | 1 491 132 A1 | 12/2004 |
| EP | 1 698 272 A2 | 9/2006 |
| EP | 1 880 657 A1 | 1/2008 |
| JP | 7-96005 B2 | 10/1995 |
| JP | 2003-93336 A | 4/2003 |
| JP | 2006-239204 A | 9/2006 |
| JP | 2006-239206 A | 9/2006 |
| WO | WO-2006/120798 A1 | 11/2006 |

OTHER PUBLICATIONS

Y. Miyake, "Analysis/Evaluation of a Digital Color Image", University of Tokyo Press, 2000, pp. 148-153.

* cited by examiner

*Primary Examiner* — Michael Won
(74) *Attorney, Agent, or Firm* — Birch, Stewart, Kolasch & Birch, LLP

(57) ABSTRACT

An electronic endoscope apparatus is provided and includes: a light source that illuminates a subject with white light; a color imaging device that takes an image of the subject illuminated with white light; and a spectral-image forming circuit that operates RGB three color image signals based on an output from the color imaging device and a matrix data to generate an spectral image signal representative of a spectral image in a color at a designated wavelength. The spectral-image forming circuit is adapted to generate spectral image signals representative of spectral images in respective colors at least three wavelengths different from one another.

3 Claims, 6 Drawing Sheets

FIG. 6

| λ1 | λ2 | λ3 |
|---|---|---|
| 400 | 500 | 600 |
| ↓ | ↓ | ↓ |
| 405 | 510 | 620 |
| ↓ | ↓ | ↓ |
| 410 | 520 | 640 |
| ↓ | ↓ | ↓ |
| 415 | 530 | 660 |
| ↓ | ↓ | ↓ |

FIG. 7

SINGLE-COLOR MODE,
SINGLE-WAVELENGTH SET

| λ1 | λ2 | λ3 |
|---|---|---|
| 470 | 470 | 470 |
| ⋮ | ⋮ | ⋮ |
| 500 | 500 | 500 |
| ⋮ | ⋮ | ⋮ |
| 530 | 530 | 530 |

ELECTRONIC ENDOSCOPE APPARATUS

BACKGROUND OF THE INVENTION

1. Field of the Invention

The present invention relates to electronic endoscope apparatuses, and more particularly to an electronic endoscope apparatus capable of forming and displaying a spectral image (video image) at a particular wavelength band by operation-processing an image signal carrying a subject color image.

2. Description of Related Art

In the field of an electronic endoscope using a solid-state imaging device, attentions are recently drawn to the apparatus for performing a spectral imaging combined with a narrow-band pass filter depending upon the spectral reflectance at a digestive organ, such as gastric mucous membrane, i.e. the electronic endoscope incorporating a narrow-band filter (narrow band imaging NBI). This apparatus has three narrow (wavelength) band-pass filters in place of the field-sequential rotary filters of R (red), G (green) and B (blue). By sequentially outputting illumination light through the narrow band-pass filters, three signals obtained based on the illumination light are processed similarly to the RGB signals while changing weighting, thereby forming a spectral image. With such a spectral image, a fine tissue, etc. unobtainable in the background art can be extracted out of a digestive organ, such as stomach or large intestine.

Meanwhile, in a synchronous type arranging fine mosaic filters on a solid-state imaging device as disclosed in JP-B-7-96005, JP-A-2003-93336 and Y. Miyake, "Analysis/Evaluation of a Digital Color Image", University of Tokyo Press, 2000, p.148-153, instead of the field-sequential type using narrow band-pass filters like the above, there is a proposal to form a spectral image by operation-processing the image signal obtained by taking an image of a subject illuminated with white light. This is to determine, as matrix data (coefficient sets), the relationship between digitized data of RGB color sensitivity characteristics and digitized data of spectral characteristics at a particular narrow band, then obtaining a spectral-image signal presuming a spectral image obtained by operating the matrix data with RGB signals through a narrow band-pass filter. Where forming a spectral image by such operation, there is no need to prepare a plurality of filters corresponding to a desired wavelength band. In addition, because of no need of exchanging those, the apparatus can be avoided from increasing its size thus reducing the cost thereof.

However, in the electronic endoscope for obtaining a spectral image through operation-processing as above, a spectral image is configured to be displayed as a monochromatic image or as a color image based on particular three colors previously designated. Despite distinction is clear between a normal region and a focal site, the region on display is possibly in a color different from the real one. In this respect, annoyance is to be felt by a physician not accustomed to using the apparatus.

SUMMARY OF THE INVENTION

An object of an illustrative, non-limiting embodiment of the invention is to an electronic endoscope apparatus arranged to obtain a spectral image by an operation, in which a spectral image in a region can be displayed similar in hue to the real one.

According to an aspect of the invention, there is provided an electronic endoscope apparatus comprising: a light source that illuminates a subject with white light; a color imaging device that takes an image of the subject illuminated with white light; and a spectral-image forming circuit that operates RGB three color image signals based on an output from the color imaging device and a matrix data to generate an spectral image signal representative of a spectral image in a color at a designated wavelength, wherein the spectral-image forming circuit is adapted to generate spectral image signals representative of spectral images in respective colors at least three wavelengths different from one another.

Incidentally, the three wavelengths are preferably wavelengths at red, green and blue portions of light.

Meanwhile, the matrix data for generating the spectral-image signal representative of the spectral image in the color at the designated wavelength can be prepared and stored in a storage section in advance.

Meanwhile, the spectral-image forming circuit may be adapted to be capable of generating a spectral-image signal representative of a spectral image in a fixed colors so as to selectively output the signal representative of the spectral image in the fixed color and the spectral image signal representative of the spectral image in the color of the designated wavelength.

BRIEF DESCRIPTION OF THE DRAWINGS

The features of the invention will appear more fully upon consideration of the exemplary embodiment of the invention, which are schematically set forth in the drawings, in which:

FIG. 6 is a figure showing a wavelength change made with a wavelength change switch of the electronic endoscope apparatus in FIG. 1; and FIG. 7 is a figure showing a wavelength set to be selected in single-color mode for the electronic endoscope apparatus in FIG. 1.

DETAILED DESCRIPTION OF THE EXEMPLARY EMBODIMENTS

Although the invention will be described below with reference to exemplary embodiments thereof, the following exemplary embodiments and modifications do not restrict the invention.

An electronic endoscope apparatus according to an exemplary embodiment of the invention is configured to generate spectral-image signals as to at least three wavelengths different one from another. Accordingly, based on the spectral-image signals, a color spectral image can be formed. Those spectral-image signals are given as signals representing spectral images in colors at designated wavelengths. Accordingly, a spectral image, displayed on a display or to be recorded at an image recorder depending upon the spectral-image signals, is to represent the region taken an image of by a color imaging device basically identically in hue to the real one.

Meanwhile, in the electronic endoscope apparatus, particularly where matrix data as in the above is previously prepared and stored in a storage section, operation processing can be performed swiftly to display or record a spectral image.

Meanwhile, in the electronic endoscope apparatus, particularly where the spectral-image forming circuit is configured to generate also a signal representative of a spectral image in a fixed color and to selectively output the signal representative of the spectral image in the fixed colors and the signal representative of the spectral image in the color at the designated wavelength, a spectral image can be desirably selectably displayed or recorded identically in hue to the real one or displayed or recorded in fixed hue in accordance with the requirement of a physician or the like.

With reference to the drawings, explanation will be now made on an exemplary embodiment according to the present invention.

Figure 1:
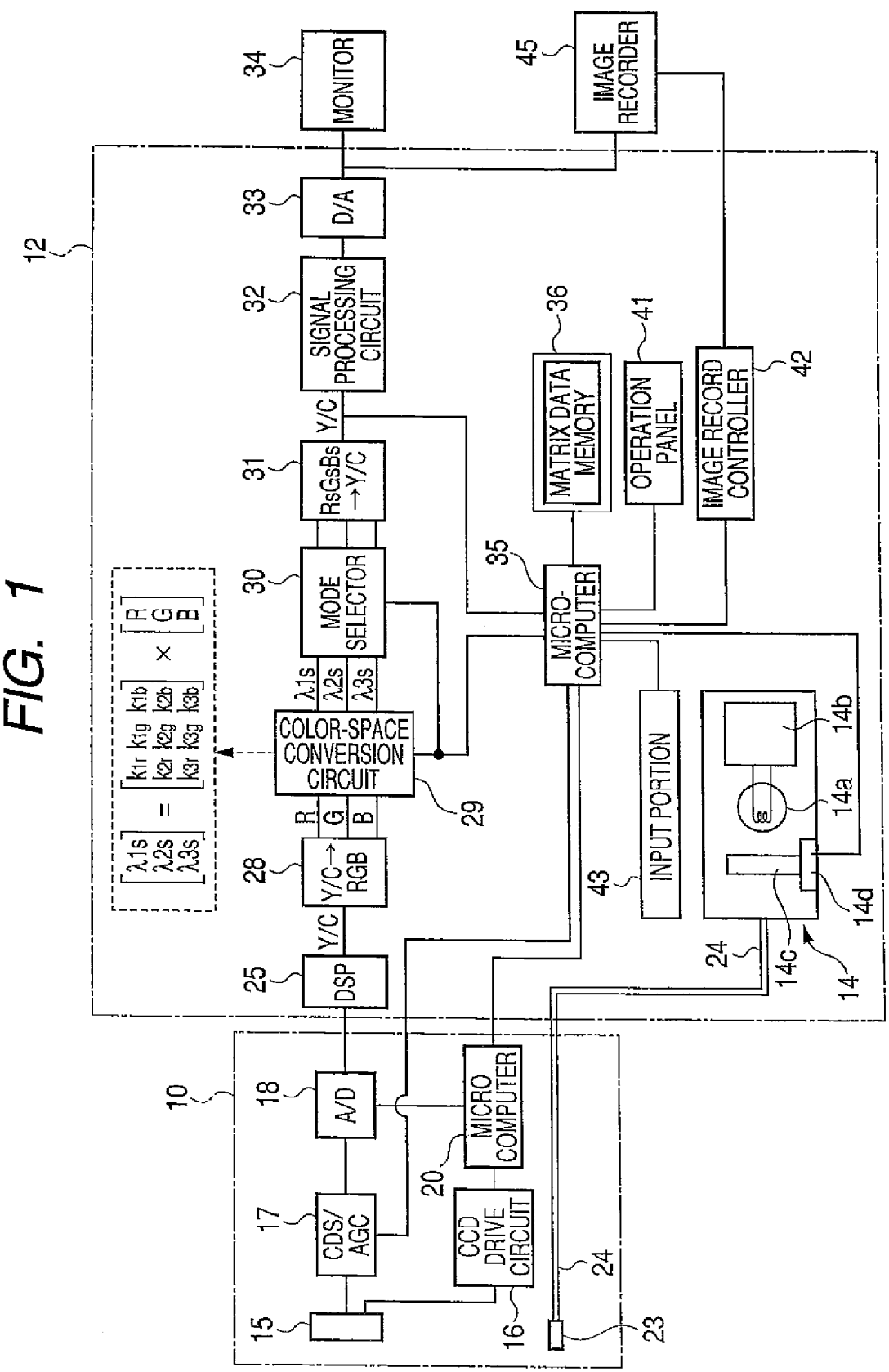
FIG. 1 is a block diagram showing a configuration of an electronic endoscope apparatus according to an exemplary embodiment of the present invention.

FIG. 1 shows a basic configuration of an electronic endoscope apparatus according to an exemplary embodiment of the invention. The electronic endoscope apparatus of the embodiment is to be set in any of a mode to display a subject spectral image formed as referred later, and a mode to display a subject ordinary image. In the spectral-image display mode, setting is selectively available in any one of a mode to display a spectral image as a color image based on fixed three color-image signals and a mode to display a color image showing a subject in a hue as per (approximate to) the actual. In the outset, explanation is made on the spectral-image display mode and the configuration for realizing same.

As shown in FIG. 1, the electronic endoscope apparatus is constructed with a scope 10, i.e. an endoscope main body, and a processor unit 12 detachably connected with the scope 10. The processor unit 12 is arranged therein with a light source 14 that emits white light. An illumination window 23 is provided at a tip of the scope 10. The illumination window 23 is opposed with one end of a light guide 24 the other end of which is connected to the light source 14. Note that the light source 14 may be arranged separately from the processor unit 12.

A CCD, or solid-state imaging device, 15 is provided at a tip of the scope 10. The CCD 15 uses a complementary-color type having Mg (magenta), Ye (yellow) and Cy (cyan) color filters or a primary-color type having RGB color filters at the image surface.

The CCD 15 is connected with a CCD drive circuit 16 that forms a drive pulse depending upon a synchronization signal, and a CDS/AGC (correlated double sampling/auto gain control) circuit 17 that samples and amplifies the image (video) signal outputted from the CCD 15. The CDS/AGC circuit 17 is connected with an A/D converter 18 that digitizes the analog output thereof. Furthermore, within the scope 10, a microcomputer 20 is provided to control the various circuits provided therein and take communication control with the processor unit 12.

Meanwhile, in the processor unit 12, a DSP (digital signal processor) 25 is provided to perform various image processes on the image signal digitized at the A/D converter 18. From the image signal, the DSP 25 is to generate and output a Y/C signal constituted by luminance (Y) and color difference [C(R−Y, B−Y)] signals. The DSP 25 is connected with a first conversion circuit 28. The first color-conversion circuit 28 is to convert the Y/C signal outputted from the DSP 25 into R, G and B three color-image signals. Note that the DSP 25 may be arranged on the scope 10 side.

In the rear stage to the first color-conversion circuit 28, there are connected in order a color-space transforming circuit 29 that performs matrix operation for forming a spectral image and outputs image signals representative of spectral images at selected wavelength bands λ1, λ2, λ3, a mode selector 30 that selects any of a single-color mode to form a spectral image at one narrow wavelength band and a three-color mode to form a spectral image at three wavelength bands, a second color-conversion circuit 31 that inputs image signals λ1s, λ2s, λ3s at one or three wavelength bands as signals Rs, Gs, Bs in order to perform a process corresponding to RGB signals and converts the signals Rs, Gs, Bs into a Y/C signal, a signal processing circuit 32 that performs signal processing including mirror image processing, mask generation and character generation, and a D/A converter 33. The D/A converter 33, in the last stage, is connected to the outside of the processor unit 12, e.g. a monitor 34 made by a liquid-crystal display, a CRT or the like and to an image recorder 45 made by a light-scanning recorder. Incidentally, in place of the three-color mode to be selected by the mode selector 30, two-color mode may be established to form a spectral image at two wavelength bands.

Meanwhile, in the processor unit 12, a microcomputer 35 is provided having a function to have communications with the scope 10, to control the circuits of the processor unit 12 and to input the matrix (coefficient) data stored in a memory 36 to the color-space transforming circuit 29 or so. The memory 36 is stored with matrix data in a table form to form a spectral image based upon RGB signals. In the embodiment, the matrix data stored in the memory 36 is exemplified as in Table 1.

TABLE 1

| Parameter | $K_{pr}$ | $K_{pg}$ | $K_{pb}$ |
|---|---|---|---|
| p1 | 0.000083 | −0.00188 | 0.003592 |
| . | . | . | . |
| . | . | . | . |
| . | . | . | . |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| . | . | . | . |
| . | . | . | . |
| . | . | . | . |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −0.000036 |
| p51 | 0.005152 | −0.00192 | 0.000088 |
| p52 | 0.005215 | −0.00207 | 0.000217 |
| . | . | . | . |
| . | . | . | . |
| . | . | . | . |
| p61 | 0.00548 | −0.00229 | 0.00453 |
| p1 | 1.00000 | 0.00000 | 0.00000 |
| p2 | 0.00000 | 1.00000 | 0.00000 |
| p3 | 0.00000 | 0.00000 | 1.00000 |

The matrix data in Table 1 is constituted with sixty-one wavelength parameters (coefficient sets) p1-p61 obtained by segmenting the wavelength range of 400 to 700 nm at an interval of 5 nm and parameters P1-P3 for forming an ordinary image. The parameters p1-p61 are each constituted with coefficients $k_{pr}$, $k_{pg}$ and $k_{pb}$ (p-1-61) while the parameter P1 is with coefficients (1.00000, 0.00000, 0.00000), the parameter P2 is with coefficients (0.00000, 1.00000, 0.00000) and the parameter P3 is with coefficients (0.00000, 0.00000, 1.00000).

In the color-space transforming circuit 29, matrix operation, shown in the following equation 1, is performed by use of the coefficients $k_{pr}$, $k_{pg}$, $k_{pb}$ and the RGB signals outputted from the first color-conversion circuit 28, to thereby form spectral image signals λ1s, λ2s, λ3s.

$$\begin{bmatrix} \lambda 1 \\ \lambda 2 \\ \lambda 3 \end{bmatrix} = \begin{bmatrix} k_{1r} & k_{1g} & k_{1b} \\ k_{2r} & k_{2g} & k_{2b} \\ k_{3r} & k_{3g} & k_{3b} \end{bmatrix} \times \begin{bmatrix} R \\ G \\ B \end{bmatrix} \quad \text{Equation 1}$$

Namely, in the case that 500 nm, 620 nm and 650 nm, for example, are selected respectively as the wavelength bands λ1, λ2, λ3 for constituting a spectral image, matrix operation is performed by using, as coefficients ($k_{pr}$, $k_{pg}$, $k_{pb}$), the coefficients (−0.00119, 0.002346, 0.0016) of the parameter p21 corresponding to the center wavelength 500 nm, the coefficients (0.004022, 0.000068, −0.00097) of the parameter p45 corresponding to the center wavelength 620 nm and the coefficients (0.005152, −0.00192, −0.000088) of the parameter p51 corresponding to the center wavelength 650 nm, of among the sixty-one parameters in Table 1.

Incidentally, the color-space transforming circuit 29 performs matrix operation by use of the coefficients of parameters P1-P3 when instructed to display or record an ordinary image. In such a case, the RUB signals outputted from the first color-conversion circuit 28 are outputted, as they are, from the color-space transforming circuit 29.

Figure 2:
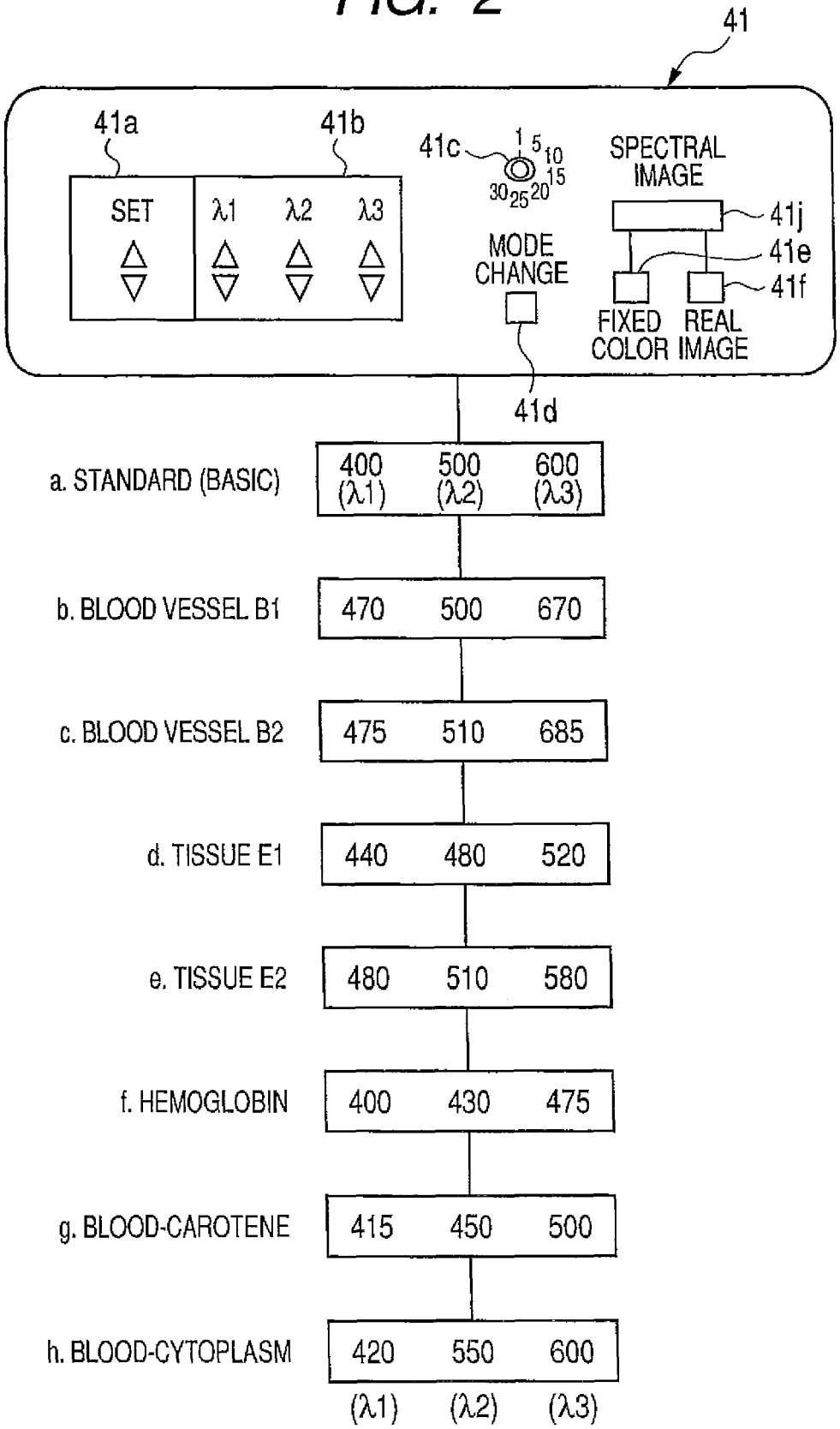
FIG. 2 is a figure showing an operation panel arrangement of a processor unit constituting the electronic endoscope apparatus in FIG. 1, with an example of wavelength set.

The microcomputer 35 is connected with an operation panel 41, an image record controller 42, and an input potion 43 such as a keyboard, in addition to the memory 36. FIG. 2 illustrates in detail the operation panel 41. The operation panel 41 is provided with a set select switch 41a for selecting any of wavelength sets a-h schematically shown together therewith, a wavelength select switch 41b for selecting respective center wavelengths of wavelength bands λ1, π2, λ3, a change-interval setting switch 41c for setting an interval of wavelength to be changed by the wavelength select switch 41b, a single-three color mode change switch for switching between single-color mode and three-color mode as mentioned before, and a spectral-image forming switch 41j for giving an instruction to form a spectral image.

Incidentally, the spectral-image forming switch 41j can be provided on the scope 10 side. Meanwhile, although a fixed-color mode switch 41e and a real-color mode switch 41f are provided in a position lower than the spectral-image forming switch 41j, those will be referred later.

Now explanation is made on the operation of the electronic endoscope apparatus according to the embodiment configured as above. In the outset, explanation is made for the case the spectral-image forming switch 41j is pressed, i.e. forming a spectral image.

In forming a spectral image, the light source 14 shown in FIG. 1 is driven to emit white light into the light guide 24. The white light, exiting at the light guide 24 arranged within the scope 10, is illuminated to a subject. The CCD 15, driven by the CCD drive circuit 16, takes an image of the subject and outputs an image signal. The image signal is subjected to correlated double sampling and auto gain control at the CDS/AGC circuit 17, and then A/D-converted at the A/D converter, thus being inputted as a digital signal to the DSP 25 of the processor unit 12.

At the DSP 25, gamma processing is made on the output signal of from the scope 10 while color conversion is made on the signals obtained through the Mg, Ye, Cy and g color filters, to form a Y/C signal as noted before. The Y/C signal, outputted from the DSP 25, is inputted to the first color-conversion circuit 28 where it is converted into an RGB signals. The RGB signals are inputted to the color-space transforming circuit 29. In the color-space transforming circuit 29, matrix operation is performed based on the RGB signals and the matrix data, in order to form a spectral image.

Now explanation is made in detail on the operation. When pressing the spectral-image forming switch 41j of the FIG. 2 operation panel 41, the color-space transforming circuit 29 performs matrix operation, for forming a spectral image, according to the equation 1 by use of the matrix data stored in the memory 36 together with the pixel-based RGB signals. Namely, in this case, three wavelength bands λ1, λ2, λ3 are established by the operation on the operation panel 41 so that the microcomputer 35 can read the matrix data corresponding to the selected three wavelength bands out of the memory 36 and then input those to the color-space transforming circuit 29.

For example, in the case that 500 nm, 620 nm and 650 nm are selected respectively as the three wavelength bands λ1, λ2, λ3, used are the coefficients of parameter p21, p45 and p51 in Table 1 corresponding to the respective wavelengths. From the pixel-based RGB signals, spectral image signals λ1s, λ2s, λs are formed according to matrix operation with the following equation 2.

$$\begin{bmatrix} \lambda 1s \\ \lambda 2s \\ \lambda 3s \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix} \quad \text{Equation 2}$$

In the case that three-color mode is selected at the mode selector 30 connected to the FIG. 2 single-three color mode change switch 41d, the spectral image signals λ1s, λ2s, λs are respectively inputted as three color image signals Rs, Gs, Bs to the second color-conversion circuit 31. Meanwhile, in the case that single-color mode is selected, any one of the spectral image signals λ1s, λ2s, λs is inputted as a signal Rs, Gs, Bs to the second color-conversion circuit 31. From now on, explanation is made in detail on the case the three-color mode is selected.

In the second color-conversion circuit 31, the three-color image signals Rs, Gs, Bs are converted into a Y/C signal (Y, Rs−Y, Bs−Y). The Y/C signal is inputted to the monitor 34 and image recorder 45 through the signal processing circuit 32 and D/A converter 33.

Figure 4:
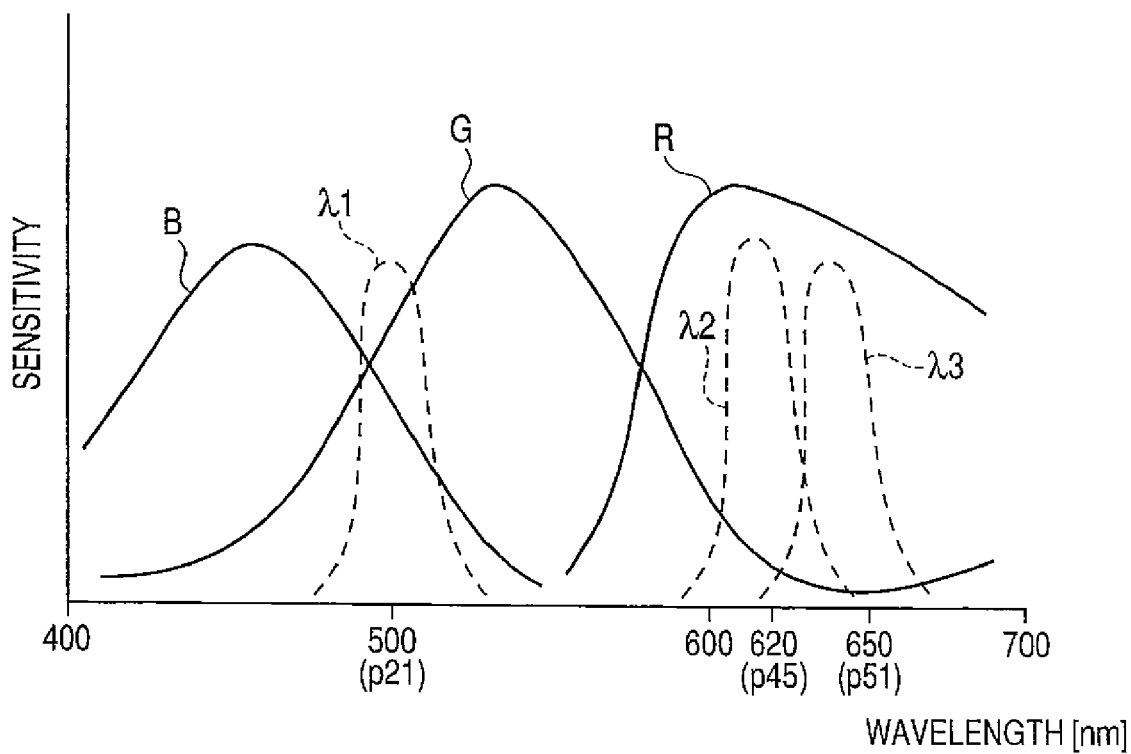
FIG. 4 is a graph showing an example of a spectral-image wavelength bands, together with a spectral sensitivity characteristic of a primary-color type CCD.
Figure 5:
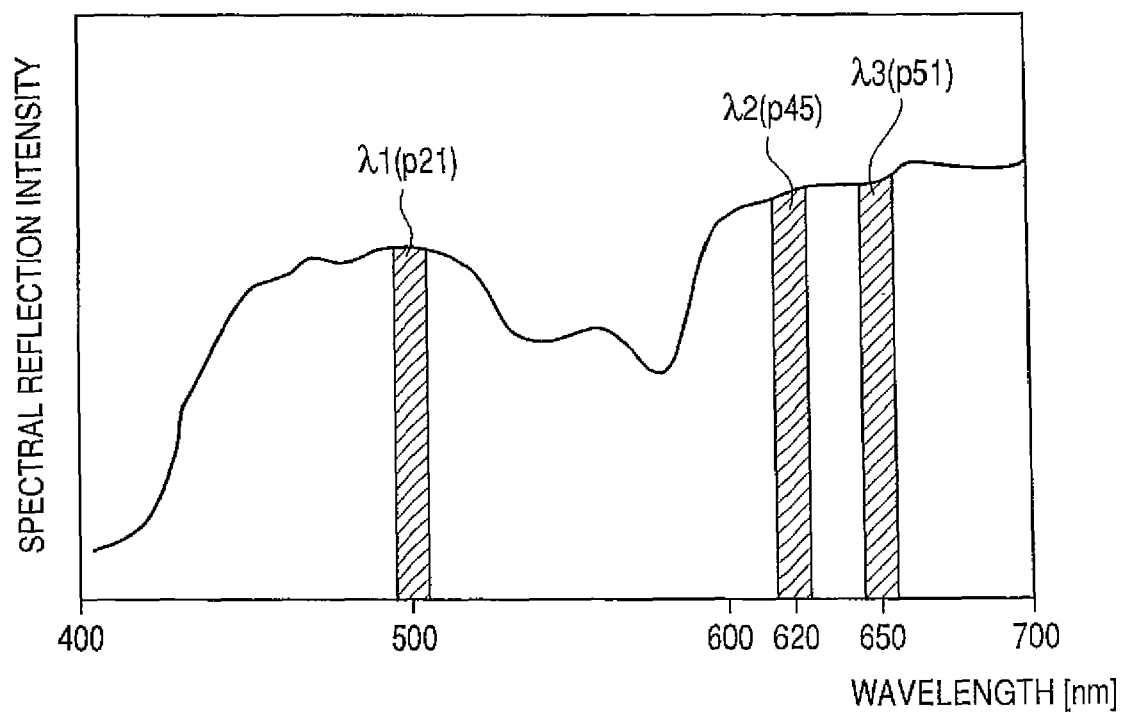
FIG. 5 is a graph showing an example of a spectral-image wavelength bands, together with a reflection spectrum of from a living body.

Based on the Y/C signal, the monitor 34 displays a spectral image given as a color image constituted by color components at wavelength bands as shown in FIGS. 4 and 5. Namely, FIG. 4 is a concept figure showing a superposition of the three wavelength bands λ1, λ2, λ3, for forming a spectral image, over color-filter spectral sensitivity characteristics R, G, B of the primary-color CCD 15. FIG. 5 is a concept figure showing a superposition of the three wavelength bands λ1, λ2, λ3 over a reflection spectrum of from a living body. The spectral image signals λ1s, λ2s, λ3s, based on the exemplified parameters p21, p45, p51, represent a spectral image having a wavelength band in a range of within ±10 nm respectively about 500 nm, 620 nm and 650 nm, as shown in FIG. 5. The three signals, in a combination, constitute a color spectral image (moving or still image) that is to be displayed or recorded.

In the case the fixed-color mode switch 41e shown in FIG. 2 is being pressed, the color spectral image is given as a color image based on fixed three color-image signals. Meanwhile, in the case the real-color mode switch 41f shown in FIG. 2 is pressed, a color image of a subject is displayed or to be recorded in a real color (in a color approximate to the actual), explanation will be made in detail later in respect of this point.

Now explanation is made on the selection of wavelength bands λ1, λ2, λ3. In this embodiment, the FIG. 1 memory 36 in its part is stored with eight wavelength sets λ1, λ2, λ3 as default, i.e. a standard set "e" at 400, 500, 600 (nm, true for the following), a blood vessel B1 set "b" at 470, 500, 670 for rendering a blood vessel, a blood vessel B2 set "c" at 475, 510, 685 also for rendering a blood vessel, a tissue E1 set "d" at 440, 480, 520 for rendering a particular tissue, a tissue E2 set "e" at 480, 510, 580 also for rendering a particular tissue, a hemoglobin set "f" at 400, 430, 475 for rendering a difference between oxy-hemoglobin and deoxy-hemoglobin, a blood-carotene set "g" at 415, 450, 500 for rendering a difference between blood and carotene, and a blood-cytoplasm set "h" at 420, 550, 600 for rendering a difference between blood and carotene.

In case the electronic endoscope apparatus after shop shipment is first booted up by powering on, the default wavelength set is selected by the microcomputer 35. When the spectral-image forming switch 41j is pressed on the operation panel 41 shown in FIG. 2, the monitor 34 in FIG. 3 displays a standard set "a" of the selected wavelength set at its wavelength-information indication area 34s. At this time, in case three-color mode is being selected by pressing the mode change switch 41d, the parameters corresponding to λ1=400 nm, λ2=500 nm and λ3=600 nm of the standard set "a" are read out of the memory 36 and inputted to the color-space transforming circuit 29. The color-space transforming circuit 29 performs matrix operation by use of the parameters thus inputted.

Meanwhile, the operator, e.g. clinical physician, is allowed to desirably select any of the other wavelength sets "b"-"h" of the default wavelength set by operating the select switch 41a of the operation panel 41 in FIG. 2. The microcomputer 35 causes the monitor 34 in FIG. 3 to display the wavelength set thus selected at its wavelength-information indication area 34s. Simultaneously, the microcomputer 35 reads the parameters corresponding to the wavelength bands λ1, λ2, λ3 of the selected wavelength set out of the memory 36 and inputs those to the color-space transforming circuit 29. The color-space transforming circuit 29 performs matrix operation by use of the parameters thus inputted.

The set select switch 41a is made up by an upper switch in which an operating portion has an upward triangular shape and a lower switch in which an operating portion has an downward triangular shape. Each time the former is pressed, wavelength set is selected in the order of "a"→"h"→"g" . . . whereas, each time the latter is pressed, wavelength set is selected in the order of "a"→"b"→"c" . . .

Meanwhile, where one of the wavelength sets "a"-"h" is being selected, the wavelength bands λ1, λ2, λ3 of the selected wavelength set can be respectively changed to desired values by operator's operation of the wavelength select switch 41b. In changing the wavelength bands, the interval of wavelength change can be varied by means of the change-interval setting switch 41c. Namely, by rotating the knob of the change-interval setting switch 41c, continuous or stepwise switchover is available e.g. at an interval of 1 nm approximate to continuous change, or at an interval of 5 nm, 10 nm or 20 nm as stepwise change. Incidentally, where switchover is at an interval of 1 nm for example, 301 wavelength bands are set up in a range of 400-700 nm, to prepare matrix data (p'1-p'301) correspondingly to the 301 wavelength bands.

FIG. 6 shows a selection of a wavelength band. At a setting of 5 nm interval, switchover is available as 400→405→410 as shown in changing λ1. At a setting of 20 nm interval, switchover is as 600→620→640 as shown in changing λ3, which value is shown on the monitor 34 at its wavelength-information indication area 34s.

Figure 3A:
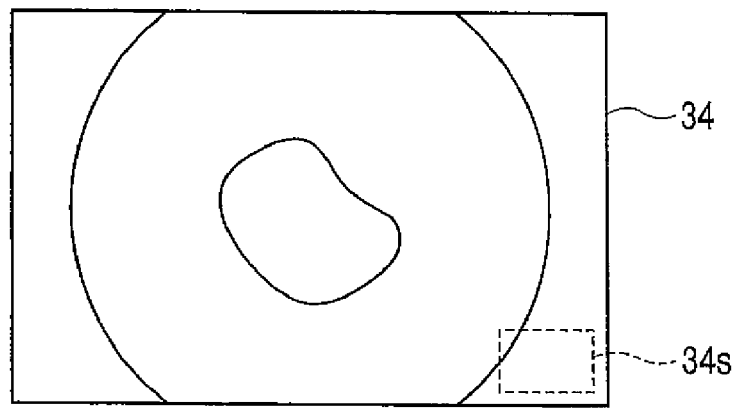
FIGS. 3A to 3C are figures showing a wavelength-information indication area on the monitor of the electronic endoscope apparatus in FIG. 1, with an indication example.
Figure 3B:
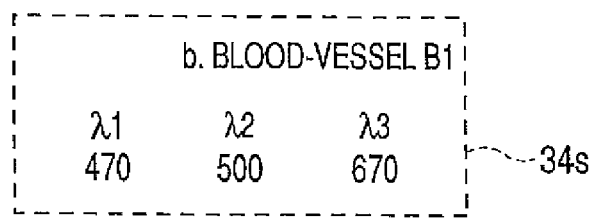
Figure 3C:
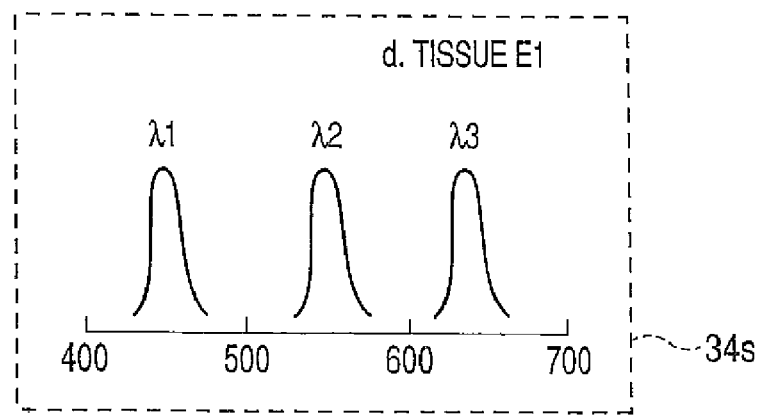

FIGS. 3A to 3C shows in detail a display state in the wavelength-information indication area 34s. In the embodiment, waveform information is to be displayed in the wavelength-information indication area 34s set up on the monitor 34 at its lower right area, as shown in FIG. 3A. Namely, in the wavelength-information indication area 34s, selected wavelength values (nm) are indicated underneath the characters λ1, λ2, λ3, etc., as shown in FIG. 3B. Alternatively, as shown in FIG. 3C, wavelength division is taken on the abscissa while sensitivity is on the ordinate so that a selected wavelength band can be visually displayed on a movable graph (correspondingly to FIG. 4).

The mode change switch 41d shown in FIG. 2 is to switch between single-color mode and three-color mode. In the three-color mode operation, pressing the mode change switch 41d provides a switchover into single-color mode so that the microcomputer 35 can set all the wavelength bands λ1, λ2, λ3 at the same value, e.g. 470, 470, 470. On the monitor 34, wavelength band common in value are displayed as shown in FIG. 7. As for such a common wavelength band, a desired value can be selected by the wavelength select switch 41b.

Here, besides the default wavelength sets mentioned before, other sets may be prepared as the foregoing eight wavelength sets in accordance with the desire, etc. of the physician who is an apparatus user so that those can be stored in the memory and selected for proper use. Meanwhile, the switches on the operation panel 41 in a part or whole function thereof may be replaced with a key function of a keyboard.

Now explanation is made on the mode to make a color display of a spectral image based on fixed three colors and the mode to make a color display of same in a real color of the subject (in a color approximate to the real one). First, the former mode is explained, i.e. the case the fixed-color mode switch 41e in FIG. 2 is being pressed. In this case, the color-space transforming circuit 29 inputs spectral-image signals λ1s, λ2s, λ3s respectively as signals Rs, Gs, Bs, corresponding to fixed colors (colors, say, at wavelengths of 400 nm, 500 nm, 600 nm), to the second color-conversion circuit 31 regardless of the wavelengths λ1, λ2, λ3. Due to this, the spectral image, displayed on the monitor 34 or to be recorded at the image recorder 45, is given as a color image configured based on the fixed three colors. Incidentally, where single-color mode is selected at the mode selector 30, a spectral-image signal λ1s, λ2s or λ3s, representative of a spectral image based on one of the fixed three colors, is inputted as an Rs, Gs or Bs signal to the second color-conversion circuit 31.

Now explanation is made on the case the 2 real-color mode switch 41f in FIG. 2 is being pressed. In this case, the color-space transforming circuit 29 inputs spectral-image signals λ1s, λ2s, λ3s respectively as signals Rs, Gs, Bs, representative of a spectral image in colors at the wavelengths λ1, λ2, λ3, to the second color-conversion circuit 31. Due to this, the spectral image, displayed on the monitor 34 or to be recorded at the image recorder 45, is indicated basically identical in hue to the real one, as to the region of the subject taken an image of by the CCD 15.

Now explanation is made in detail on the generation of spectral-image signals λ1s, λ2s, λ3s for realizing such real-color mode. In the foregoing fixed-color mode, the color-space transforming circuit 29 outputs the spectral-image signals λ1s, λ2s, λ3s, formed by matrix operation according to equation 2, respectively as three-color image signals Rs, Gs, Bs carried with light intensities in colors at wavelengths of 400 nm, 500 nm and 600 nm (in a image display case). On the contrary, in the real-color mode, provided that Rs, Gs and Bs are also carried with light intensities in colors at wavelengths of 400 nm, 500 nm and 600 nm for example, the color-space transforming circuit 29 outputs spectral-image signals λ1s, λ2s, λ3s respectively formed by the following operations.

$$\lambda 1s = aRs + bGs + cBs$$

$$\lambda 2s = dRs + eGs + fBs$$

$$\lambda 3s = gRs + hGs + iBs$$

The above nine coefficients "a"-"i" are defined as per the following and stored in a table form based on each combination of wavelengths λ1, λ2, λ3, say, in the memory 36. In operation, those are read out by the microcomputer 35 and inputted to the color-space transforming circuit 29. Provided that the coefficients "a"-"i" are properly defined based on each combination of wavelengths λ1, λ2, λ3, then the spectral image, displayed on the monitor 34 or to be recorded at the image recorder 45, is indicated basically identical in hue to the real one as to the region of the subject taken an image of by the CCD 15.

Now explanation is made on the method to determine the coefficients "a"-"i". It is herein considered that, provided that the tristimulus values (X, Y, Z) are identical with using color-matching functions, the image in a portion to display on the monitor 34 is displayed identical in hue to the real one. From now on, vectors are assumed shown in lower cases while matrixes in upper case. The color-matching functions at a wavelength λ is assumed given as:

$$\bar{x}(\lambda), \bar{y}(\lambda), \bar{z}(\lambda), \text{ and} \qquad \text{Equation 3:}$$

the colors on the monitor 34 is as:

$$\bar{r}(\lambda), \bar{g}(\lambda), \bar{b}(\lambda). \qquad \text{Equation 4:}$$

Furthermore, the chromaticities at the three wavelengths λ1, λ2, λ3 are assumed respectively as $(x_1, y_1, z_1)$, $(x_2, y_2, z_2)$ and $(x_3, y_3, z_3)$.

At the equal chromaticity value, human eye is to visually perceive the color equivalent. Accordingly, in case the following expression is held with the nine coefficients "a"-"i", the monitor 34 displays an image at its portion identical in hue to the real one.

$$\begin{pmatrix} \bar{x}(\lambda) \\ \bar{y}(\lambda) \\ \bar{z}(\lambda) \end{pmatrix} (\bar{r}(\lambda)\bar{g}(\lambda)\bar{b}(\lambda)) \begin{pmatrix} a & d & g \\ b & e & h \\ c & f & i \end{pmatrix} = \begin{pmatrix} x_1 & x_2 & x_3 \\ y_1 & y_2 & y_3 \\ z_1 & z_2 & z_3 \end{pmatrix} \qquad \text{Equation 5}$$

Here, $$(\bar{x}(\lambda)\bar{y}(\lambda)\bar{z}(\lambda)) = A \qquad \text{Equation 6}$$

$$r(\bar{r}(\lambda)\bar{g}(\lambda)\bar{b}(\lambda)) = B$$

$$\begin{pmatrix} a & d & g \\ b & e & h \\ c & f & i \end{pmatrix} = C$$

$$\begin{pmatrix} x_1 & x_2 & x_3 \\ y_1 & y_2 & y_3 \\ z_1 & z_2 & z_3 \end{pmatrix} = D$$

If representing transposition with "~", $$\tilde{A}B\ C = D \therefore C = (\tilde{A}\ B)^{-1} D, \text{ and}$$

$$\tilde{A}\ B \qquad \text{Equation 8:}$$

is given as 3×3 thus resulting in the existence of an inverse matrix.

Accordingly, based on the known A, B and D, coefficient matrix C (namely, coefficients "a"-"i") can be determined as:

$$C = (\tilde{A}\ B)^{-1} D. \qquad \text{Equation 9:}$$

However, Equation 10: C does not include a negative element. Hence, coefficients "a"-"i" are determined by forcibly taking as 0 (zero) the negative element resulting from calculation.

Incidentally, the explanation so far was made on the case to display or record a color image based on three-color image signals λ1s, λ2s, λ3s. In the case of displaying or recording a color image based on four or more colors of image signals, it is possible to form signals representing a spectral image identical in hue to the real one basically on the basis of the similar way of thinking.

Now explanation is made on the mode to display an ordinary image of a subject. In the case the spectral image forming switch 41j on the operation panel 41 in FIG. 2 is pressed again when displaying a spectral image formed in the foregoing manner or the spectral image forming switch 41j is not pressed from the beginning, the parameter P1-P3 coefficients are selected for matrix operation at the color-space transforming circuit 29. Due to this, the color-space transforming circuit 29 outputs the RGB signal, which the first color-conversion circuit 28 outputted, without change. The RGB signal is converted into a Y/C signal at the second color-conversion circuit 31. The Y/C signal is inputted through the signal processing circuit 32 and D/A converter 33 onto the monitor 34. The monitor 34 displays thereon an ordinary color image (moving or still image) of the subject.

Incidentally, in the embodiment, the output of the D/A converter 33 is inputted to the image recorder 45 besides to the monitor 34. When the image-record controller 42 under control of the microcomputer 35 instructs the image recorder 45 to record an image, the image recorder 45 outputs an ordinary color image of or a spectral-image hard copy of a scene as designated by the instruction.

Incidentally, with the conventional endoscope, it is a practice to disperse a coloring agent, such as indigo or pyoktanin to the subject and take an image of a tissue colored by the dispersion. On the contrary, by selecting, as a set of wavelengths λ1, λ2, λ3, wavelength bands at which to be rendered is a tissue colored by dispersing a coloring agent, it is possible to obtain a spectral image equivalent to that due to coloring-agent dispersion without dispersing a coloring agent.

Although description has been given heretofore of the invention with reference to the above-mentioned embodiments and examples, the invention is not limited to such embodiments and examples but various modifications are also possible. For example, the values of the radii of curvature, surface intervals and refractive indexes of the respective lens components are not limited to the values that are shown in the above-mentioned numerical examples, but other values can also be used. Also, in the above-mentioned embodiments and examples, the both surfaces of the first to fourth lenses are all formed as aspherical surfaces; however, the invention is not limited to this.

This application claims foreign priority from Japanese Patent Application No. 2006-267104, filed Sep. 29, 2006, the entire disclosure of which is herein incorporated by reference.

What is claimed is:

1. An electronic endoscope apparatus comprising:
   a light source that illuminates a subject with white light;
   a color imaging device that takes an image of the subject illuminated with white light; and
   a spectral-image forming circuit that operates RGB three color image signals based on an output from the color imaging device and a matrix data to generate a spectral image signal representative of a spectral image in a color at a designated wavelength, wherein the spectral-image forming circuit is adapted to generate spectral image signals representative of spectral images in respective colors of at least three wavelengths different from one another;
   wherein the spectral-image forming circuit is adapted to be capable of generating another spectral-image signal representative of another spectral image in a fixed color so as to selectively output either (i) the spectral image signal representative of the spectral image in the fixed color or (ii) the spectral image signal representative of the spectral image in the color of the designated wavelength.

2. The electronic endoscope apparatus according to claim 1, further comprising a storage section that stores the matrix data.

3. The electronic endoscope apparatus according to claim 1, wherein the at least three wavelengths includes wavelengths at red, green and blue portions of light.

* * * * *